United States Patent [19]

Newhouse

[11] Patent Number: 5,113,855
[45] Date of Patent: May 19, 1992

[54] POWDER INHALER

[76] Inventor: Michael T. Newhouse, 436 Queen Street South, Hamilton, Ontario, Canada, L8P 3T9

[21] Appl. No.: 484,069

[22] Filed: Feb. 14, 1990

[51] Int. Cl.⁵ ............................................ A61M 15/00
[52] U.S. Cl. ........................... 128/203.12; 128/203.15
[58] Field of Search ...................... 128/203.15, 203.21, 128/200.14, 203.12; 604/58

[56] References Cited

U.S. PATENT DOCUMENTS

| | | | |
|---|---|---|---|
| 2,570,774 | 10/1951 | Davis | 128/203.15 |
| 2,579,280 | 12/1951 | Trumbour et al. | 128/203.15 |
| 2,581,182 | 1/1952 | Fields | 128/203.15 |
| 2,587,215 | 2/1952 | Priestly | 128/203.15 |
| 4,274,403 | 6/1981 | Struve | 128/203.15 |
| 4,534,343 | 8/1985 | Nowacki et al. | 128/203.15 |

Primary Examiner—Edgar S. Burr
Assistant Examiner—Aaron J. Lewis
Attorney, Agent, or Firm—Robert M. Wolters

[57] ABSTRACT

A powdered medication inhaler is provided which comprises a body having a hollow chamber of substantial height. Powdered medication is transferred from a hopper by a dosing blade having an amperture therein to a transfer station opening into a chamber. In most embodiments of the invention the transfer station is adjacent the upper portion of the chamber, but in one embodiment it is adjacent the lower portion thereof. When the transfer station is adjacent the upper portion of the chamber it includes a pallet or cup on which powdered medication is dropped or blown from the dosing blade. Gas then carries the medication from the cup or pallet into the chamber for inhalation by a patient. In the embodiment in which the transfer station is adjacent the bottom of the chamber compressed gas blows the powder up into the chamber.

22 Claims, 5 Drawing Sheets

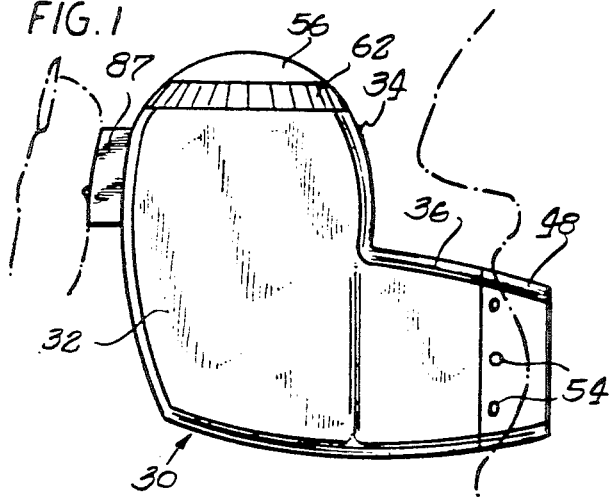
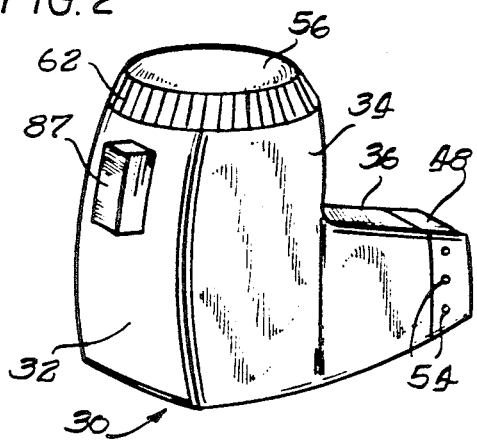
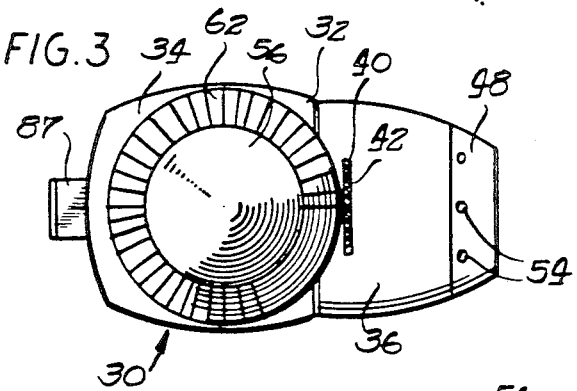
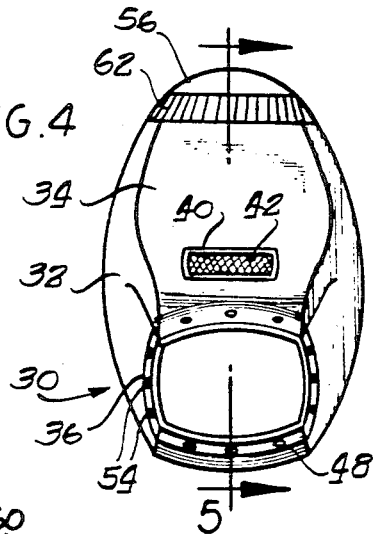
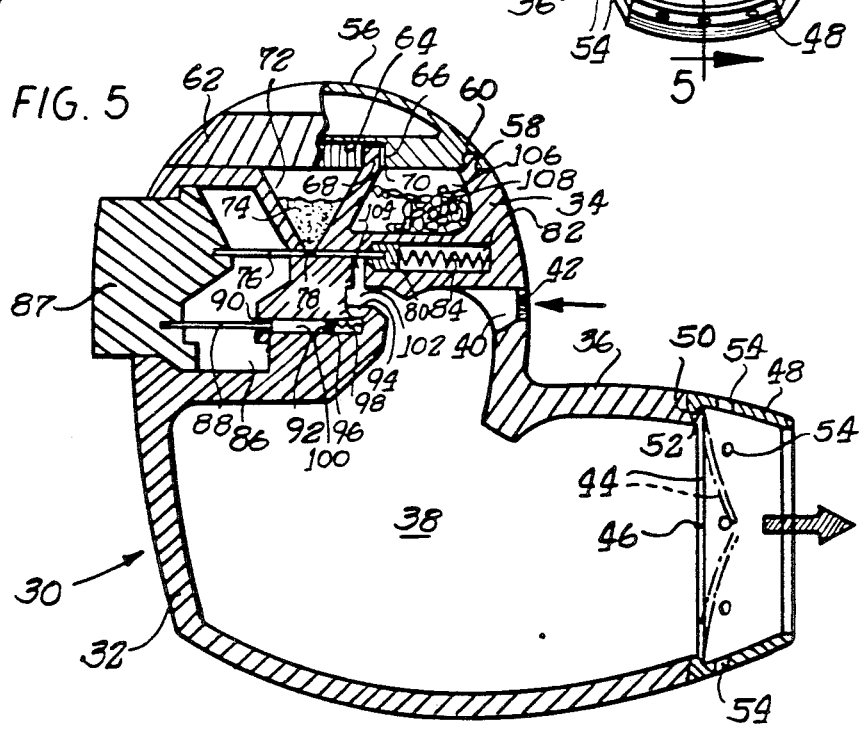

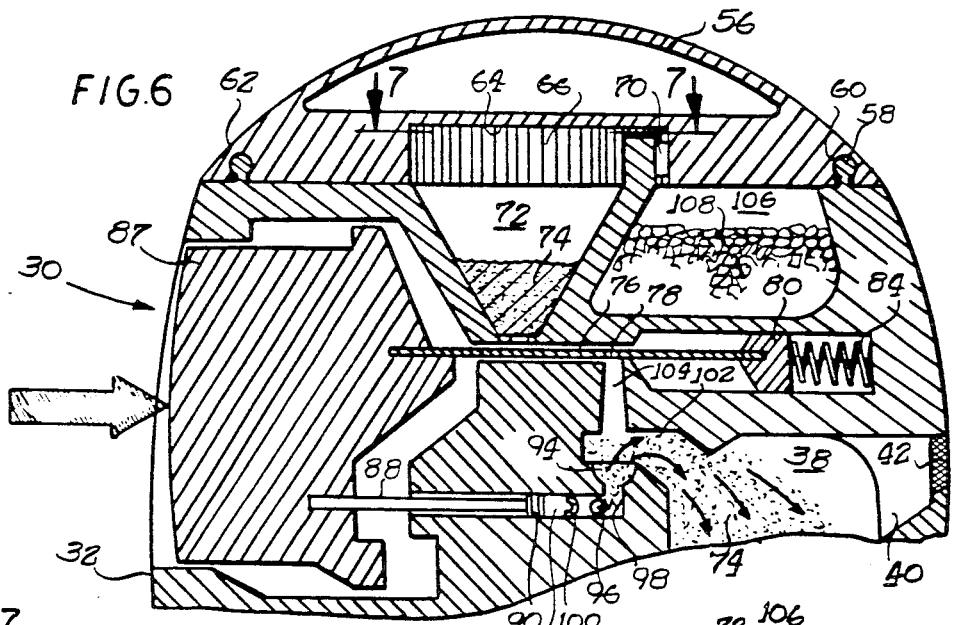
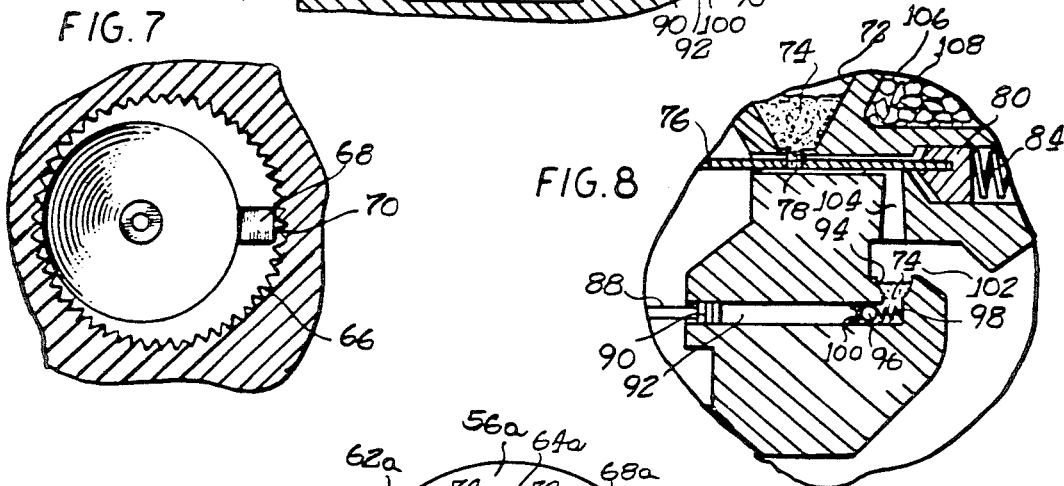
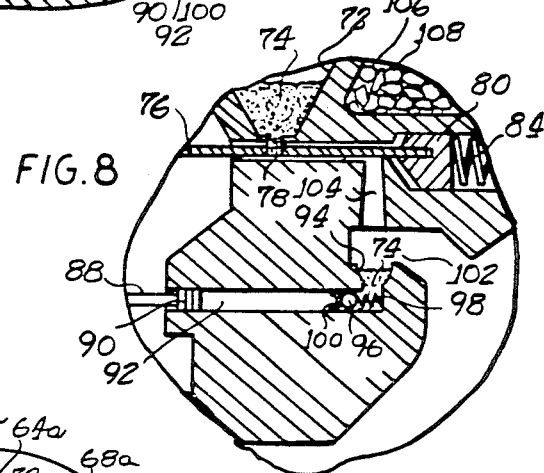
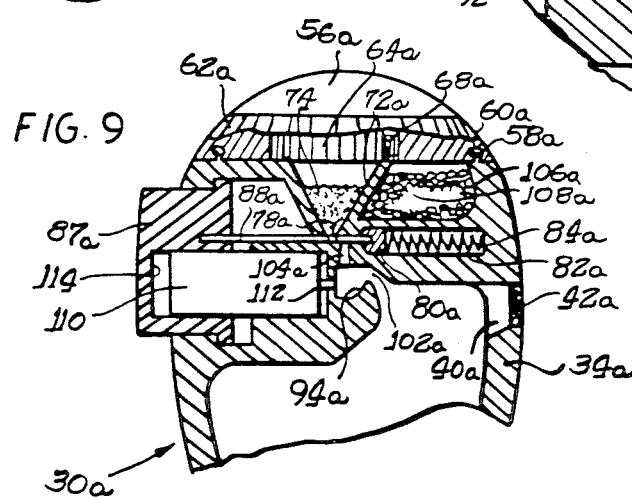

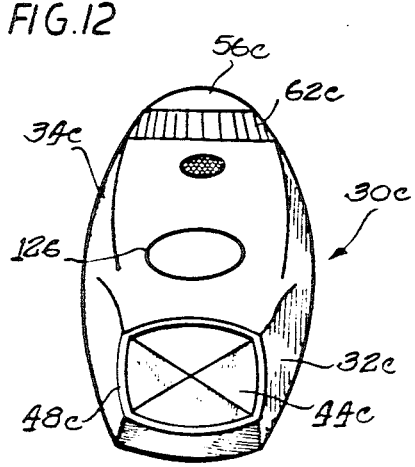
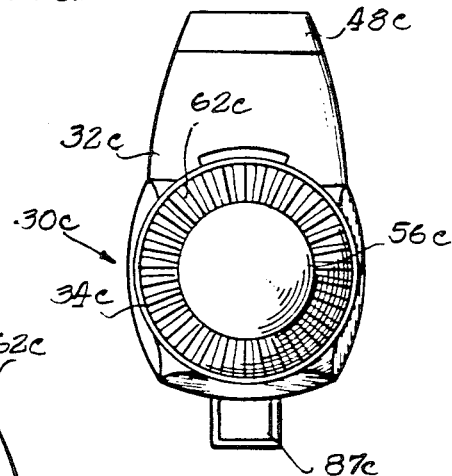
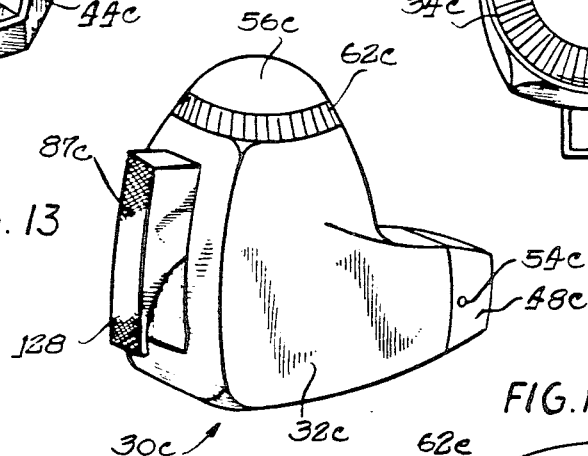
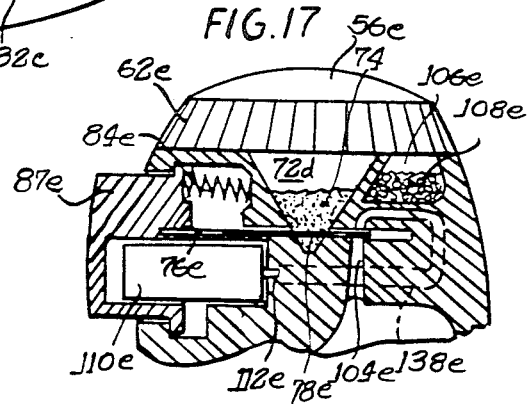
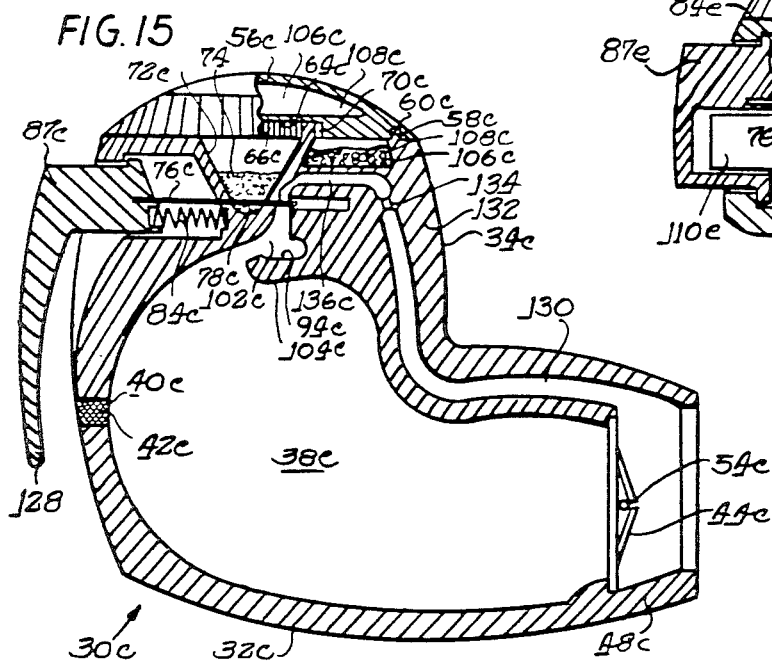

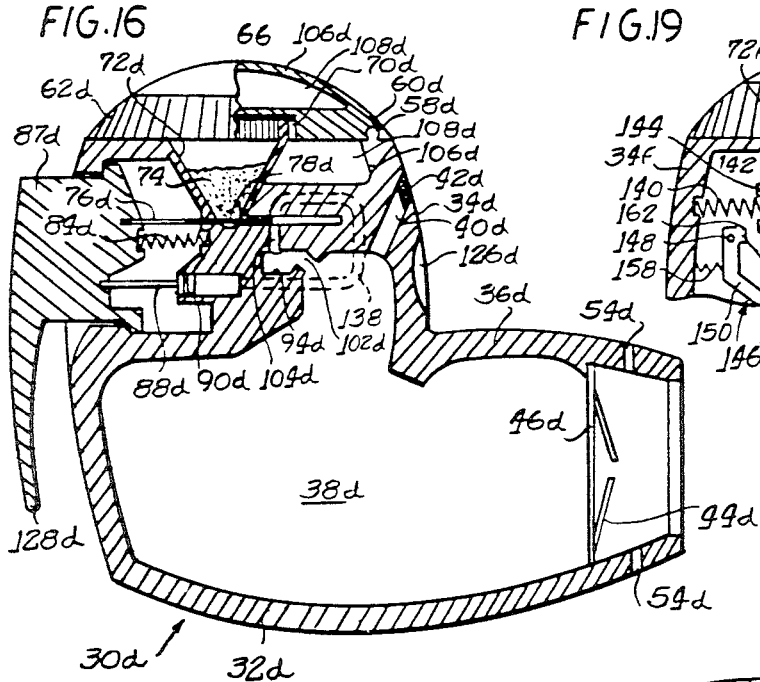
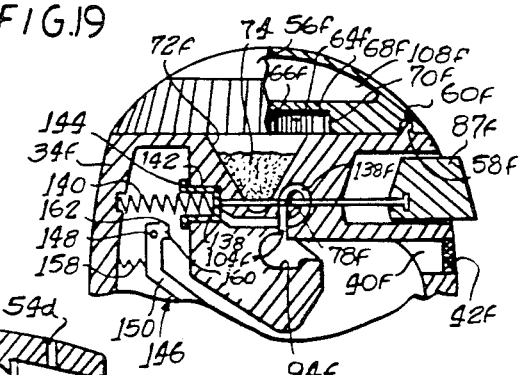
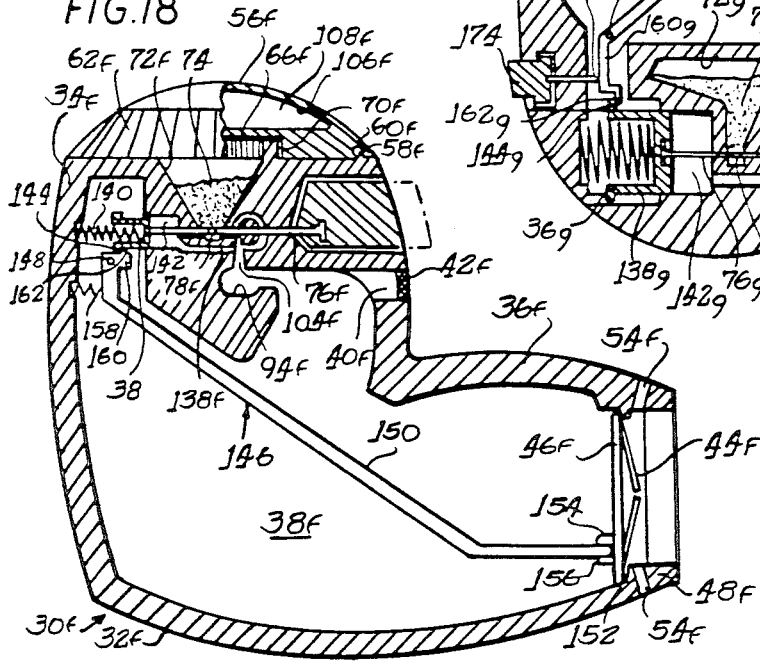

POWDER INHALER

BACKGROUND OF THE INVENTION

Patients suffering from asthma or any of many other lung diseases require delivery of medication to the bronchi or to the lungs. At the present time, there are two major ways of delivering aerosol treatment or medication to such patients, namely nebulizers, which may be of the venturi-jet type, or of the ultrasonic type which produce aerosols from drug solutions, and metered dose inhalers consisting of pressurized canisters containing Freon and the drug, or alternatively, powder inhalers.

Metered dose inhalers in general are superior to nebulizers, because they are readily portable, they do not require an external power source such as compressed air or electricity, and they are capable of generating aerosols that are suitable for inhalation.

The problem with Freon driven units is that hydrofluorocarbons are being limited in quantity, or phased out, because of their effect on the upper ozone layer.

Existing powder inhalers may use unit doses consisting of small cartridges or capsules which are in some way broken open so that the powder can be inhaled. Alternatively, there are some devides that may contain multiple doses in a small hopper, and a metering system to assure that each dose is similar. These latter devices are generally superior in that they are activated by the patient's inhalation, rather than by Freon.

Up to the present time, the inhalers that have been the most popular have been those that consist of a Freon pressurized canister containing the drug particles. These devices generate a droplet aerosol consisting of Freon and the drug particles. The Freon evaporates rapidly, and leaves small drug particles of about three microns aerodynamic mass median diameter available for inhalation. Thus, aerosol particles are made available to patients, not only for maintenance treatment, but also for extremely ill patients who have very little inspiratory flow rates. However, with the current unpopularity of hydrofluorocarbons, continuing efforts have been made to utilize crystalline powders of the drug material without the need to use a pressurization system containing Freon.

There are some currently available powder inhalation systems, but they do not function effectively unless the patient can generate flow rates over approximately 20-30 liters per minute, since it is the patient's inhalation that mobilizes the powder and prepares it for inhalation, in contrast to the metered dose inhaler which uses Freon to mobilize the powder. The problem of such current powder inhaler systems is that they require strong inhalation on the part of the patient. Accordingly, they may be useful for maintenance treatment of patients with chronic bronchitis, emphysema and asthma, but they not work effectively or at all in people with severe asthma attacks, or those who have deterioration of their chronic bronchitis or emphysema related to respiratory infections.

Objects and Summary of the Present Invention

Accordingly, it is an object of the present invention to provide a powder inhaler which provides for a metered dose of medication to be inhaled by a patient, and which does not require high inspiratory effort by the patient.

More particularly, it is an object of the present invention to provide a powder aerosol inhaler in which the powder aerosol generation is completely separated from inhalation.

More particularly, it is an object of the present invention to provide a powder aerosol inhaler as set forth above in which a measured or metered quantity of powder is blown into an inhalation chamber, and is then inhaled easily by the patient.

In accordance with the present invention a hand held unit is provided which, as sold, includes sufficient powdered medication for 200-400 doses. A metered dose of powder is transferred from a storage area to a dispensing area, and then is blown into a relatively large volume chamber by various means hereinafter to be described. The powdered dispersed in the chamber then is readily inhaled by the patient without requiring a high inspiratory rate by the patient.

THE DRAWINGS

The invention will best be understood from the following specification when studies with the accompanying drawings wherein:

FIG. 1 is a side view of a powder inhaler in accordance with the present invention;

FIG. 2 is a perspective view of the inhaler of FIG. 1;

FIG. 3 is a top view thereof;

FIG. 4 is an end view thereof;

FIG. 5 is a longitudinal sectional view of the inhaler of FIGS. 1-4 on an enlarged scale;

FIG. 6 is a further enlarged section of a portion of the device in FIG. 5 showing parts in a different position of operation;

FIG. 7 is a fragmentary horizontal sectional view taken substantially along the line 7—7 in FIG. 6;

FIG. 8 is a fragmentary longitudinal sectional view similar to a portion of FIG. 6, but showing the parts in a somewhat different position of operation;

FIG. 9 is a framgentary longitudinal view similar to a portion of FIG. 5, but showing a modification;

FIG. 12 is an end view of a modification of the invention, generally similar to FIG. 4;

FIG. 13 is a perspective view similar to FIG. 3, showing the modification of FIG. 12;

FIG. 14 is a top view of the modification of FIG. 12, generally similar to FIG. 3;

FIG. 15 is a longitudinal sectional view similar to FIG. 5, showing the modification of FIG. 12;

FIG. 16 is a longitudinal sectional view similar to FIG. 15, showing a further modification of the invention;

FIG. 17 is a fragmentary sectional view similar to a portion of FIG. 16, showing yet another modification of the invention;

FIG. 18 is a longitudinal sectional view of a further modification of the invention;

FIG. 19 is a fragmentary view similar to a portion of FIG. 18, with the parts in a different position of operation; and FIG. 20 is another longitudinal sectional view of a modification of the invention, generally similar to that in FIG. 18, but essentially turned upside down to be less obtrusive.

DETAILED DISCLOSURE OF THE ILLUSTRATIVE EMBODIMENTS

Figure 10:
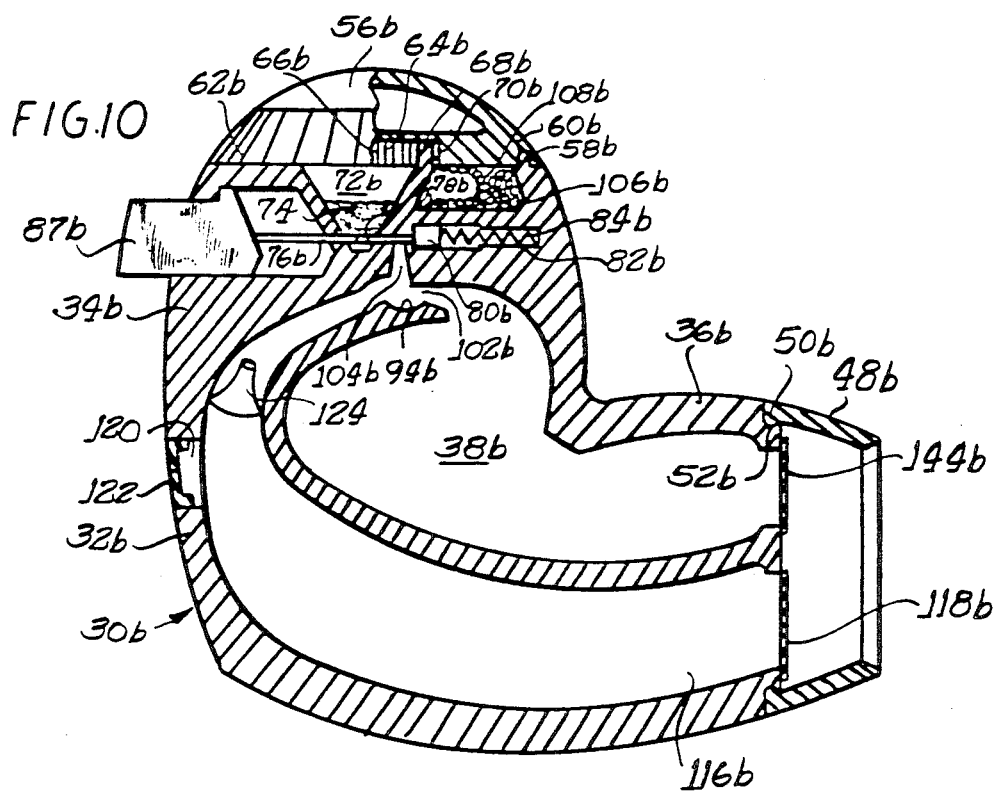
FIG. 10 is a longitudinal sectional view generally similar to FIG. 5, but showing a modification of the invention.

A powder inhaler 30 constructed in accordance with the principles of the present invention is shown in FIGS. 1-8, and attention should first be directed to these figures. The inhaler 30 includes a molded plastic body 32 having an upstanding chimmey-like portion 34, and a lateral portion 36. The interior of the body has a generally L-shaped cavity comprising an aerosol settling and holding chamber 38. An inlet opening 40 extends through the wall of the upstanding portion and is provided with a filter screen 42. The opening 40 and filter screen 42 are shown as generally rectangular in FIG. 4, but other shapes could be used. The lateral portion 36 opens outwardly from the chamber 38 and is provided with a one-way flap valve 44 having a spider or other backing device 46 to permit air movement outwardly from the chamber 38, but not into the chamber. Such valves are known in the art, and one satisfactory valve is shown in U.S. Pat. No. 4,470,412. A mouthpiece 48 extends from the lateral portion 36 (to the right in FIG. 5), being secured on the lateral portion by an inward protuberance 50 on the mouthpiece received in a peripheral indentation 52 adjacent the end of the extension 36. The mouthpiece is open at both ends, and further is provided with a plurality of peripheral bores 54 to accommodate exhalation. When the patient places a mouthpiece in his mouth and exhales, the valve diaphram 44 will be pressed firmly against the backing member, whereby no air can enter the chamber 38. The exhaled air is dispersed through the openings 54. On the other hand, when the patient inhales, the valve diaphram deflects to the right as shown in FIG. 5 in broken lines, and air enters the opening 40 through the screen 42 into the chamber 38, and out through the valve and the mouthpiece. A relatively small amount of air will enter into the mouthpiece through the holes 54 during inhalation, since the total area of these holes is substantially less than the total area of the opening 40.

A top cap or dome 56 overlies the upstanding portion 34 of the body, and is rotatably secured thereto by an upstanding ridge 58 at the top of the body received an annular recess 60 on the underside of the lid 56. The projection or rib 58 snaps into the recess 60, so that the lid does not fall off, and so that the lid is not readily removed by the user. The periphery of the exterior of the lid is ribbed or serrated at 62 to permit rotation of the cap by the user.

The underside of the cap is provided with a central recess 64 having a vertical circumferential wall 66 (see particularly FIG. 7), the inner surface of which is striated or serrated vertically. An upstanding member 68 extends into the recess 64, and is provided with a radially outwardly projecting tooth 70. When the cap is manually rotated the serrations of the sidewall 66 successively ratchet over the tooth 70 to cause a certain amount of vibration. This vibration will serve to keep the powdered medication (to be discussed shortly hereinafter) loose and free of caking.

Directly beneath the cap 56 the top of the upstanding portion 34 is provided with a conical hopper 72 having its apex downwardly directed and slightly truncated. This hopper is provided at the factory with a predetermined quantity of medication powder 74.

An elongated flat strip or plate 76 extends across the apex of the hopper and forms a dosing blade. The blade preferably is made of steel. The blade is provided with a through-bore 78 which initially aligned with the apex of the hopper 72. The right end of the blade extends to a piston or spring abuttment 80 in which it is secured. The spring abuttment 80 is received in a cylindrical bore 82 in which a helical spring 84 is housed, pressing at one end against the end of the cylinder 82, and at the other end against the spring abuttment 80, and thus normally to hold the dosing blade 76 in the position shown in FIG. 5.

At the outwardly extending face of the chimney or upwardly extending portion 34 (upper left in FIG. 5) there is a cavity 86 in which there is mounted a finger operating button 87 which extends outwardly of the inhaler body 32. The right or inner end of the chamber or cylinder 86 is of somewhat irregular shape, as shown, to accommodate to other interior portions of the body, including the hopper 72. The outer or left end of the dosing blade 76 is secured in a facing portion of the button 87. There is also a piston rod 88 secured in the inner portion of the button 87 and extending horizontally to the right in FIG. 5. A small piston 90 is fixed on the end of the piston rod 88 and is movable in a horizontal cylinder 92. There is an upward opening at the far right end of the cylinder 92 forming a cup or pallet 94. A valve ball 96 is disposed in the cylinder relatively near the right end thereof, and is pressed to the left by a spring 98, being limited by a ball stop 100.

Directly above the cup or pallet 94 there is a lateral extension 102 of the chamber 38. Extending upwardly from the lateral extension 102 there is a vertical bore 104 which is closed at the top end by the dosing blade 76, relatively adjacent the piston or spring abuttment 80.

A chamber 108 is disposed to the right of the hopper 74, and opens at the top into recess 64. Silicagel 108 is disposed in this chamber at the factory for helping to keep the medication power 74 dry.

Operation of the powder inhaler will best be understood with reference to FIGS. 5, 6 and 8. Parts are shown in stand-by position in FIG. 5. The dosing blade 76 will be understood as comprising a transfer means and the hole or bore 78 therein will be understood as comprising a medicine transfer recess therein. In this position the hole or bore 78 through the dosing blade 76 is aligned with the apex of the hopper 72 and receives gravitationally powder medication from the hopper. At the same time the piston 90 is in retracted position. The ball 96 sits against the retainer 100. The fragmentary view of FIG. 8 shows the parts in the same position as FIG. 5, but on an enlarged scale. The patient places the mouthpiece 48 in his mouth substantially as shown in FIG. 1, and exhales. The flap valve 44 will not permit exhaled air to enter the chamber 38, but passes out through the lateral holes 54. The patient then depresses the button 87 with his finger, and the hole 78 in the dosing blade moves into alignment with the shaft or passageway 104. As will be appreciated, the hole 78 carries a measured dose of powdered medication and this drops through the shaft 104 to the cup or pallet 94, the shaft 104 and the cup or pallet 94 thus constituting a powdered medication discharging station. At the same time the piston 90 is moved to the right. The ball is initially held in closing position to the left by the spring 98, about the time the powder has been dumped from the dosing blade to the cup or paliet, the ball unseats to the right from the pressure developed in the cylinder 92, and a puff of air passes up through the cup or pallet to carry powdered medication in somewhat dispersed fashion at 74' to the right and into the aerosol settling and holding chamber into which it drops gravitationally, providing further dispersal of the powder. The patient then inhales the powder.

A modification of the invention in shown in FIG. 9. Most parts are similar to those previously described, and similar numerals with the addition of the suffix a are used to identify like parts, thereby avoiding repetition of description. The powdered medication remains the same, and is again identified by numeral 74. The distinction is that the piston 80 and cylinder 92 arrangement is replaced by a gas canister 110 having an outlet valve 112. The left end of the canister as shown in FIG. 9 is spaced from a confronting surface 114 of the pushbutton. After a certain amount of lost motion to allow the dosing blade to transfer medication to the cup or pallet 94a the surface 114 engages the end of the canister and shifts it slightly to the right, forcing the valve nozzle 112 against a stop, thereby releasing a metered quantity of gas.

Since the gas is used physically as a propellant, it need not be Freon, and generally would be carbon dioxide, oxygen, or nitrogen, all of which are a part of the atmosphere, and would not cause any problems with the ozone layer.

Figure 11:
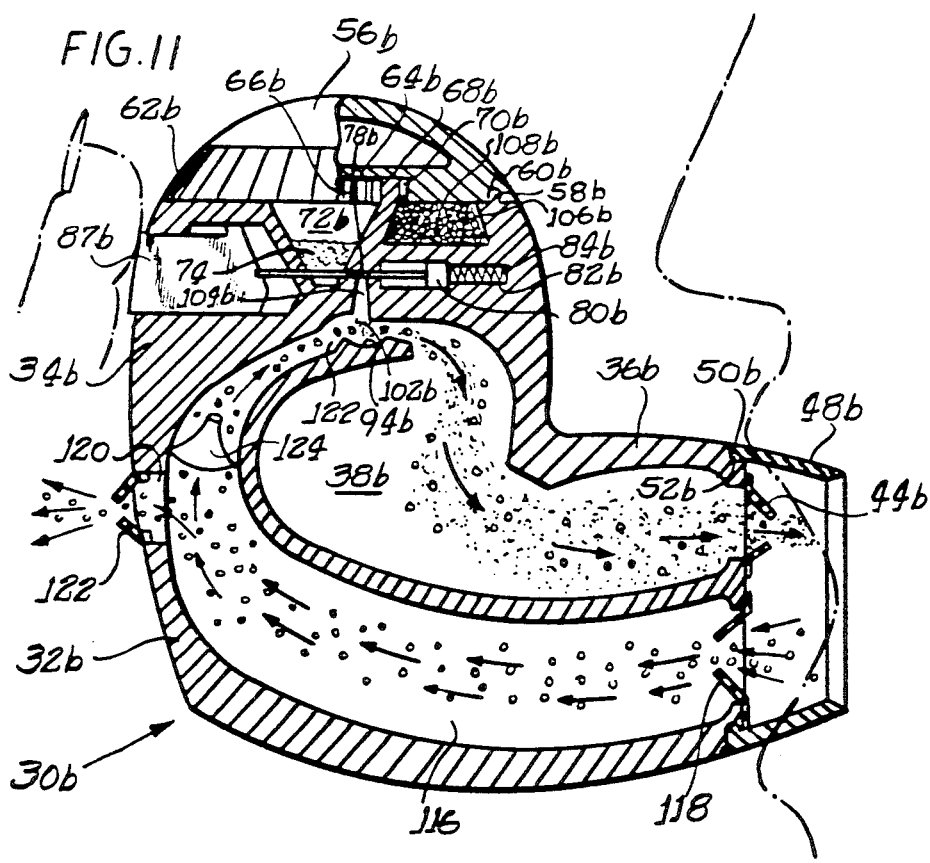
FIG. 11 is a sectional view similar to FIG. 10 but showing the parts in a different position of operation.

A further embodiment of the invention is shown in FIGS. 10 and 11. Many of the parts are the same as or similar to parts heretofore shown and described, and such parts are identified by the same numbers with the addition of the suffix b. The medication powder again is identified with the numeral 74, since it does not change. The mouthpiece 48b does not have exit holes therein corresponding to the holes 54 in the previous embodiments. There is no piston operated by the pushbutton 87b, and the aerosol settling and holding chamber 38b is smaller than the one previously disclosed. There are important distinctions. The chamber 38b exits through the mouthpiece through an inhalation flap valve 44b which may be similar to the valve 44 heretofore disclosed. No backing member or spider is specifically shown but one may be provided unless the flaps of the valve are so constructed and arranged as to move in only one direction.

Below the chamber 38b there is an exhalation chamber 116 which opens into the mouthpiece 48b through an inhalation valve 118. This valve may be similar to the flap valves heretofore discussed, and will open only to the left, and not to the right. The exhalation channel 116 narrows as it progresses and at the outer portion of the housing 32b there is an opening 120 closed an exhalation flap valve 122 which will allow to pass out of the channel 116 to the outside, but will not allow outside air to push the valve in the opposite direction to pass air into the channel. The extremity of the channel 116 as identified at 118 becomes quite narrow and exits across the cup or pallet 94b, passing through the opening 102b into the aerosol settling and holding chamber 38b.

A funnel-like restricting device 124 is provided in the channel 116 above the valve 122 and opening 120 to aid exhaled air flow, particularly adding velocity thereto.

To use the powderd inhaler as shown in FIGS. 10 and 11 the patient places the mouthpiece in his mouth as shown generally in FIG. 11. The patient exhales. This causes exhaled air to pass through the valve 118, the valve 44b being closed. Some of the exhaled air exits through the valve 122, but some of it passes through the restricting device 124. Meanwhile, the patient has depressed the button 87b with his finger, causing powdered medication to be blown from the cup or pallet as indicated at 74', dissipating in the chamber 38b. The patient then promptly inhales, thus closing the valve 118 and opening the valve 44b so that the aerosolized medication powder 74' is drawn into the patient's bronchi and lungs.

A modification of the invention is shown in FIGS. 12-15. Most of the parts are similar to those heretofore shown and described and are identified by similar numerals with the addition of the suffix c. Externally, the shape is changed only slightly, and a thumb recess 126 is provided at the intersection between the horizontally projecting portion 32c and the upstanding portion 34c to provide for more firm gripability of the inhaler. The operating button 87c is provided with a depending handle 128 for multi-fingered use in depressing the pushbutton. The mouthpiece 48c is formed integrally with the remainder of the inhaler.

The inhalation opening 40c is moved to an outward position below the finger button 87c and handle 128a, again being provided with a filter 42c. The aerosol settling and holding chamber 38c is generally similar to that heretofore shown and described but is somewhat different in that it is somewhat enlarged toward the outer end (left end in FIG. 15), and opens from the left through the restricted space 102c to the cup or pallet 94c. The dosing blade 86c again is provided with an opening 78c for carrying a measured dose of powdered medication from the reservoir 72c to a position aligned with the opening 104c to drop the medication powder on to the cup or pallet 94c. In the present instance a restoring spring 84c acts directly on the pushbutton 87c, rather than through the intermediary of the dosing blade.

There is additionally an exhalation channel 130 leading from inside the mouthpiece 48c up to an exhalation opening 132, and beyond that to a restriction 134 leading to a channel 136 terminating directly above the dosing blade 76c.

In operation, the patient depresses the thumb button 87c and handle 128 with one or more fingers, thereby moving the dosing blade to the right from the position shown in FIG. 15. The opening 78c through the dosing blade is of somewhat conical configuration, being larger at the bottom than at the top. When this opening moves into alignment between the channels 136 and 104c upon complete depression of the pushbutton the patient exhales. Much of the exhaled air exits through the opening 132, but a part of it passes through hole 178 in the dosing blade, and down on to the cup or pallet 94c to disperse the powder into the chamber 78c where it spreads out and settles to some extent. During this time the flap valve 44c closes and some of the exhaled air exits through two exit openings 54 at the junction of the mouthpiece and the remainder of the inhaler. Immediately following exhalation to start dispersal of the powder the patient inhales. Air enters through the opening 40c and filter 42c, and the flap valve 44c opens. The aerosolized powder is thus drawn in through the patient's mouth to the bronchi and lungs.

A further modification of the invention is shown in FIG. 16. Most of the parts are again similar to those heretofore shown and described, and like parts are again identified by similar numerals, this time with the addition of the suffix d. In this case exhalation is not required to disperse the medication powder. Rather a piston 90d operated by a piston rod 88d in the pushbutton 87d compresses air that passes through a convoluted channel 102*d* which terminates directly above the dosing blade in line with the channel 104*d* leading down to the cup or pallet 94*d*. Thus, when the dosing blade 76*d* has been moved to the right by the pushbutton 87*d* to bring the opening 74*d* into alignment with the channel 104*d* the powder in the opening 74*d* drops toward the cup or pallet, but is also propelled by compressed air through the channel 138 to send the medication powder off the cup or pallet out into the chamber 38*d* where it is moved through the valve 44*d* by inhalation.

A modification of the invention as shown in FIG. 17 is generally similar to the embodiment of FIG. 16, but embodies a gas cartridge 110*e* similar to that in FIG. 9. By the time the button 87*e* has been moved far enough to align the powder carrying opening 78*e* of the dosing blade 76 with the exit end of the convaluated channel or passageway 138*e* and the channel 104*e* the lost motion between the button and the cartridge 110*e* has been taken up and a measured quantity of gas is released from the cartridge and passes through the convoluted channel 138*e* to pass through the blade opening 78*e*, and thus to propel the medication powder into the chamber 38*e* for inhalation.

The embodiment of the invention shown in FIGS. 18 and 19 is generally similar to those heretofore shown and described, but is somewhat more automatic in operation. The finger button 87*f* would now be operated by the thumb, since it is on the opposite side of the upright portion of the body 32*f* of the inhaler 30*f*. In this embodiment similar parts are again identified by similar numerals, this time with the addition of the suffix f. The dosing blade 76*f* is secured to the pushbutton 87*f* at one end of the blade. At the other end of the blade there is a hollow piston 138 having a biasing spring 140 mounted therein and bearing against the opposite wall of the upper portion 34*f* of the body, and movable in a piston 142. The piston has a radial skirt or flange 144 at its opened end. The cylinder 162 opens into the entering end of the convoluted ducts or passageway 138*f*.

In addition, there is a lever 146 pivoted near its upper end on a pivot 148, and having a long arm which extends down from the pivot 148, then diagonally through the chamber 38*f*, and finally horizontally to a position adjacent the valve 44*f*. The backing member or spider 46*f* of the valve is not fixed in position, but is pivoted at its lower edge on a pivot 152. The backing member 46*f* has an extending flange or arm 154 that overlies the outer end 156 of the long arm 150. A spring 158 bearing against the long arm at the bottom of the vertical portion thereof downwardly from the pivot 148 to tend to pivot the lever counterclockwise, this movement being limited by engagement of the extremity 156 of the arm with the arm or flange 154 on the valve backup member 46*f*. The lever 146 further has a short arm 160 extending substantially horizontally to the right from the pivot 148. The short arm has an upwardly extending tooth 162 capable of engaging behind the perpherial skirt or flange 144 on the piston 138 as shown in FIG. 18, thus to hold the piston in retracted position.

To use the embodiment of the invention illustrated in FIGS. 18 and 19 the patient inserts the mouthpiece 48*f* in his mouth or tightly against his lips, with the mouth open. The pushbutton 87*f* is then depressed from the initial position of FIG. 19 to the position of FIG. 18. This cocks the spring 140, the piston 138 being held in retracted position by the tooth 162 on the short arm 160 of the lever 146. The hole or opening 78*f* in the dosing blade 76*f* thus is in the medicated powder and picks up a measured quantity thereof. The patient then exhales. This closes the flap valve 44*f* and causes it to press against the backing member 46*f*, thereby pivoting the backing member to the left about its pivot 152. This causes the arm or flange 154 on the backing member to lower the extremity 156 of the lever 146, thereby retracting the tooth 162 from the skirt 144 of the piston 138. The piston then moves rapidly to the right, carrying the measured quantity of medication powder into alignment between the exit end of the convoluted passageway 138*f* and the vertical passageway 104*f* leading to the cup or pallet 94*f*. At the same time air is compressed in the piston 142 and blows against the falling powder, thereby dispersing it into the chamber 38*f*. The patient inhales and the powder passes through the valve 44*f*, through the mouth, and into the bronchi and lungs.

The silicagel desiccant has been moved from the chamber in the body to a chamber in the rotary top in FIGS. 18 and 19. In FIGS. 15 and 16 it is shown in both locations, and it certainly could be in the lid or cap in any of the embodiments shown herein.

A further embodiment is shown in FIG. 20 which is generally similar to FIGS. 18 and 19, but with the parts inverted. Thus, the portion 34*g* extends downwardly rather than upwardly. The dispersing area in this case is at the bottom rather than the top, and the cylinder 142*g* communicates rather directly through a passageway 138*g* with a substantially vertical passagway 136 into which the medicine powder is dropped from the hole 78*g* in the dosing blade 76*g*. A somewhat sinuous passageway 168 extends up from the dropping area 166 into the aerosol and settling chamber 38*g*. Spiral baffles 170 are provided in the sinuous passageway 168 to break up possible clumps of drug particles into the smaller and more respirable particles. The spiral baffles somewhat jut into the sinuous passageway 168, but do not by any means occlude yet.

A stop 172 is provided to limit movement of the flap valve backing member 46*g* from its rest position. The biasing spring 158*g* bears against the long arm 150*g* of the lever 146*g* adjacent its extremity 156*g* rather than near the pivot as in FIG. 18.

Another feature to be noted in FIG. 20 is a release button 174 on the outer or remote side of the inhaler 30*g* relative to the mouthpiece 48*g*. This pushbutton 174 has an extending rod 176 which abutts the short end 160*g* of the lever 146*g*. Thus, the lever can be pivoted manually by depression of the button 174 to release the piston 138*g* for moving the dosing blade to the right to position the measured amount of medication powder between the channels 166 and 168 while simultaneously pushing compressed air therethrough to blow the powder up into the chamber 38*g*.

The hole 78*g* in the dosing blade is somewhat smaller in diameter than the upper channel portion 166 and the channel 168. This increases the velocity of the air passing therethough, thereby helping to break up the powder better and to blow it well up into the chamber 38*g*.

The upside down configuration of FIG. 20 would appeal to many people more than the previous embodiments, since it would be less obtrusive to the patient who would be holding most of the device in the palm of his hand, thus hiding it from view. Pushing of the drug or medication up into the holding chamber by the compressed air may have a certain advantage, because if the particles are spread well up into the holding chamber, they have twice as far to fall back under the influence of gravity before reaching the floor of the holding chamber. Therefore, more of the particles will be respirable for a longer period of time. (Particles of about 3 microns settle at about 0.3 mm/sec.)

In some instances the manual release pushbutton 174 has marked advantages. This is particularly suitable for infants and young children who might not be able to follow directions for exhaling to release the piston. A mask could couple the inhaler to an infant's face, and a third party, such as the infant's mother could cock the system by depressing the pushbutton 87g, and then release the medication with the trigger button 174.

The metered dose inhaler aerosol delivery system in the many embodiments herein shown as described provides for delivery of precise and reproducible doses of a variety of micron particle aerosol medications to patients with airway and possible pulmonary parenchymal diseases. It could also be used as a delivery system for drugs targeted to the lungs and systemic circulation that might be inactivated if given by mouth (e.g. proteins such as alpha₁antritrypsin, gammainterferon, insulin heparin, etc.).

The powder inhaler as disclosed herein does not require any Freon. It is easy to use, and it is pocketable, being only slightly larger than current metered dose inhalers. For example, a present inhaler would be on the order of three inches long, slightly less than three inches high, and about an inch and one-half wide. It is suitable for use by adults and children, and it is packaged with many doses in it to be dispensed one dose at a time. It requires minimal coordination on the part of the user. The aerosol generation is independent of inhalation, and the aerosol delivery many be fully breath actuated. Low inspiratory flow actually improves delivery efficiency and makes medication available even during attacks of severe airflow obstruction, such as an asthmatic attack. A pure drug substance without a diluent is delivered over a variety of dose ranges, depending on the perimeters established during manufacture. The system is particle selective and targets the lower respiratory tract and lung parenchyma and minimizes oropharyngeal, laryngeal and systemic side affects.

In certain of the embodiments of the invention herein shown and described patient exhalation aerosolizes the medication powder from the medication cup. This is perhaps the simplest method, but it does have some disadvantage in that the inside of the inhaler would become humid, and with hydroscopic particles could increase particle size and clumping. This would reduce the efficiency of lower respiratory tract deposition. Furthermore, if the patient is having an acute attack it might not be possible for him to exhale with sufficient vigor to aerosolize the powder. In other forms of the invention a piston provides compressed air to disperse the aerosol powder, or alternatively a compressed air cylinder provides about 1 cc per actuation to disperse the aerosol powder at the time of inhalation.

Full breath actuation (with manual override if needed and for administration to infants and children) is accomplished by a mechanical linkage to the flap valve backing member or support disk. In the configuration shown exhalation releases the cocked compressed air piston and also moves the dosing disk comprising the hole in the dosing blade. Thus when the dose of powder has been carried to the opening into the holding chamber, air pressure will force the powder out of the dosing disk and disperse it in the particle selective holding chamber. This removes the larger particles and clumps that would impact on the throat and vocal cords. This component of the aerosol dose is not useful for therapy, but does contribute to side effects. On inhalation the flap valve opens to make the medication available to the patient's pulmonary airways.

The drug reservoir or hopper is intended to contain 200 to 400 doses of medication, or more if necessary. The serrations in the chamber in the cap ratchet move the tooth disposed against them to set up a high frequency vibration that helps to keep the drug powder dispersed. It reduces the problem of caking. Desiccating gel preferably is placed adjacent to the drug reservoir in one position or another, as disclosed to minimize the chance of problems relating to high humidity and drug hygroscopicity.

The presence of a valve and exhalation port in the mouthpiece prevents the medication from being dispersed if the patient exhales before inhaling.

The specific examples of the invention as herein shown as described will be understood for illustrative purposes only. Various changes will no doubt occur to those skilled in the art, and will be understood as coming within the scope of the present invention insofar as they fall within the scope of the appended claims.

The invention is claimed as follows:

1. A powdered medication inhaler comprising a hollow body having a chamber of substantial height for aerosolizing and settling powdered medication, means for admitting air into said chamber, means for connecting said body and said chamber to a living body for inhalation from said chamber into said living body, a storage hopper in said hollow body for storing powdered medication and having a discharge opening therefrom, a powdered medication discharge station opening into said chamber, transfer means having a medication transfer recess therein, said transfer means being in communication with said medication storage hopper through said discharge opening, said transfer means being movable from a position with said recess communicating with said discharge opening for receiving a predetermined quantity of powdered medication in said recess to a position communicating with said discharge station, said discharge station further comprising a pallet positioned beneath said discharge opening for gravitational passage of powdered medication from said recess to said pallet, said pallet being positioned above said living body connecting means, and means adjacent said pallet operatively connected to a source of gas under pressure for positively passing gas past said discharge station and said pallet in timed relation to delivery of powdered medication to said discharge station to carry powdered medication into said aerosolizing and settling chamber for gravitational settling toward said living body connecting means for inhalation of said medication into said living body.

2. A powdered medication inhaler as set forth in claim 1 and further including manually operable means connected to said transfer means for operation thereof.

3. A powdered medication inhaler as set forth in claim 1 wherein said transfer means comprises a substantially flat dosing blade movable substantially in its own plane.

4. A powdered medication inhaler as set forth in claim 2 wherein said transfer means comprises a substantially flat dosing blade movable substantially in its own plane.

5. A powdered medication inhaler as set forth in claim 1 wherein said discharging station includes a substantially vertical passageway for receiving powdered medication from said recess.

6. A powdered medication inhaler as set forth in claim 5 and further including support means below said substantially vertical passageway for receipt of powdered medication from said recess, and wherein the means for passing gas past said discharging station includes means for passing gas across said support means to carry powdered medication into said chamber.

7. A powdered medication inhaler as set forth in claim 6 in which powdered medication passes gravitationally from said recess to said support means.

8. A powdered medication inhaler as set forth in claim 6 and further including means for passing said gas through said vertical passageway whereby said powdered medication is transferred gravitationally and by gas pressure from said recess to said support means.

9. A powdered medication inhaler as set forth in claim 5 wherein said transfer means comprises a blade, and the recess therein comprises an opening through said blade, and further including means for directing gas through said blade opening and through said vertical passageway.

10. A powdered medication inhaler as set forth in claim 9 wherein said discharge station and said vertical passageway are adjacent the upper portion of said chamber with said vertical passageway opening into said chamber adjacent the top thereof.

11. A powdered medication inhaler as set forth in claim 9 wherein said discharge station and said vertical passageway are disposed adjacent the lower portion of said chamber, and gas carries said powdered medication up through said vertical chamber and said vertical passageway into the lower portion of said chamber.

12. A powdered medication inhaler as set forth in claim 6 wherein said support means is disposed adjacent the upper portion of said aerosolizing and settling chamber and wherein gas moves past said support means to carry powdered medication into said chamber relatively adjacent the top thereof for aerosolization and settling of the powdered medication in the chamber.

13. A powdered medication inhaler as set forth in claim 12 wherein the gas passing means includes means for passing the gas horizontally past said support means.

14. A powdered medication inhaler as set forth in claim 5 wherein said transfer station is disposed adjacent the bottom of said chamber, and wherein the means for passing gas past said discharging station comprises means for passing gas upwardly to carry powdered medication into said chamber.

15. A powdered medication inhaler as set forth in claim 2 and further including support means disposed below said passageway for receipt of powdered medication from said recess, and wherein manually operating means is interconnected with said gas passing means to provide gas to said discharge station to carry powdered medication into said chamber.

16. A powdered medication inhaler as set forth in claim 15 wherein the gas passing means includes a piston.

17. A powdered medication inhaler as set forth in claim 15 wherein the gas passing means includes a cylinder of compressed gas.

18. A powdered medication inhaler as set forth in claim 5 wherein said gas passing means includes an exhaust passageway for transmitting exhaled air to said discharging station to carry powdered medication into said chamber.

19. A powdered medication inhaler as set forth in claim 1 wherein said gas passing means includes a piston, and means for cocking and releasing said piston to provide gas to said discharging station.

20. A powdered medication inhaler as set forth in claim 19, and further including means operated by exhaled air to release said piston.

21. A powdered medication inhaler as set forth in claim 19 and further including manually operable means for releasing said piston.

22. A powdered medication inhaler as set forth in claim 20 and further including manually operable means for releasing said piston.

* * * * *